US00PP07982P

United States Patent [19]

Hanes

[11] Patent Number: Plant 7,982

[45] Date of Patent: Sep. 22, 1992

[54] GERANIUM NAMED AMERICANA SCARLET

[75] Inventor: Mitchell Hanes, Morgan Hill, Calif.

[73] Assignee: Goldsmith Seeds, Inc., Gilroy, Calif.

[21] Appl. No.: 677,466

[22] Filed: Mar. 29, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

[57] ABSTRACT

A new Geranium cultivar distinguished by its scarlet flowers on large umbels; the plant itself being fast-rooting and vigorous growing to a height of 16–18 cm. as a potted plant.

1 Drawing Sheet

BACKGROUND OF THE NEW PLANT

The present invention comprises a new and distinct cultivar of Geranium, botanically known as *Pelargonium hortorum* Bailey, and hereinafter referred to by the cultivar name Americana Scarlet. The new cultivar is a hybrid seedling resulting from my controlled crossing of a red single flower female parent and a salmon colored semi-double pollen parent in the company nursery in Gilroy, Calif., this new Geranium plant being a product of a planned breeding program intended to create new Geranium cultivars with scarlet colored flowers, semi-double flower form, green foliage, vigorous growth and superior cutting productivity.

The new cultivar was developed in 1988 at Gilroy, Calif. and has been repeatedly reproduced by cuttings in Gilroy, and in Guatemala over a two year period. It has also been trialed at Okemos, Mich. It has been found to retain its distinctive characteristics through successive generations and this novelty appears to be firmly fixed.

DESCRIPTION OF THE DRAWING

This new Geranium plant is illustrated by the accompanying photographic drawing which shows blooms, buds, and foliage of the plant in full color, the colors show being as true as can be reasonably obtained by conventional photographic procedures.

DESCRIPTION OF THE NEW CULTIVAR

The following detailed descriptions set forth the distinctive characteristics of Americana Scarlet. The data which defines these characteristics were collected from asexual reproductions carried out in Gilroy, Calif. The plant history was taken on 30 week old plants, blossomed under natural light in a greenhouse and color readings were taken in the greenhouse (in Gilroy, Calif.) on May 29, 1990 at 2:00 p.m. under ambient light. Color references are primary to The R.H.S. Colour Chart of The Royal Horticultural Society of London, England.

THE PLANT

Classification:

*Botanical.*—*Pelargonium hortorum* Bailey.

*Commercial.*—Zonal Geranium.

Form: Upright, well branched.

Height: 16 to 18 cm., as a 5½ inch potted plant, excluding blooms.

Growth: Strong and fast-rooting.

Strength: Strong growth that is upright and the plant produces many flowers, good shipping ability as rooted or unrooted cuttings.

Foliage: Abundant quantity.

*Leaves.*—Size: Diameter about 7.5 cm. Shape: Rounded cordate with occasional upfolding between veins. Margin: Irregularly crenate. Texture: Leathery and pubescent on both surfaces, especially along veins.

*Ribs and veins.*—Distinctly palmate, 2.8 to 4.5 cm. long. Color: Upper side: Green with a slightly darker green zone. Underside: Lighter green color. Ribs and veins not prominently different from upper surface.

*Petioles.*—About 7.5 to 8.5 cm. in length.

THE BUD

Size:

*Diameter.*—About 6 mm.

*Length.*—About 1.7 cm. at time of bud opening.

Shape: Pointed ovoid.

Color: When sepals first divide, RHS 45-B.

Sepals: Five in number, flat behind petals. Pointed linear lanceolate, RHS 143-B in an open flower.

THE FLOWER

Blooming habit: Continuous throughout the year.

Size: Approximately 4.7 cm. diameter, 0.5 cm. deep, irregularly radially symmetrical.

Form: Cup-shaped when bloom first opens, later flattening to shallow cup-shape with maturity.

Petals: Five imbricate outer petals, 1.5–2.2 cm. wide and approximately 2.3 cm. long. Two to three inner smaller petaloids of varying shape. Both the outer petals and inner petaloids are scarlet, RHS 40-A, and fading lighter to the outer margin. Veins not much darker than interveinal regions. Color changing little with age. Underside of petals lighter. Petals and petaloids soft and satiny.

Pedicel: Approximately 2.6 cm. in length.

Persistence: Nonshattering flower.

INFLORESCENSE

Type: An umbel composed of approximnately 30 flowers, erect or laterally ascending.

Peduncle: Approximately 8–13 cm. in length, and green with a very light reddish tint on the side facing the sun.

REPRODUCTIVE ORGANS

Stamens:

*Anthers.*—Five to nine positioned below the mature stigma, dull red prior to anthesis.

*Filaments.*—White near base with an orange streak starting at mid length extending to the point of the anther attachment.

*Pollen.*—Orange in color.

Pistil:

*Number.*—One.

*Length.*—Approximately 7 mm.

*Style.*—Length: About 3 mm. Color: Purplish-red.

*Stigma.*—Five (sometimes six) linear lobes of near equal length, curling back toward ovary, purplish-red.

*Ovaries.*—At anthesis, densely pubescent with white hairs, oblong. Green drying to a light brown at maturity.

Fruit: Partially fertile.

I claim:

1. A new and distinct cultivar of Geranium plant substantially as herein shown and described characterized by green foliage, scarlet flower color, and semi-double flowers on large umbels, the plant is fast-rooting and has a very vigorous growth habit.

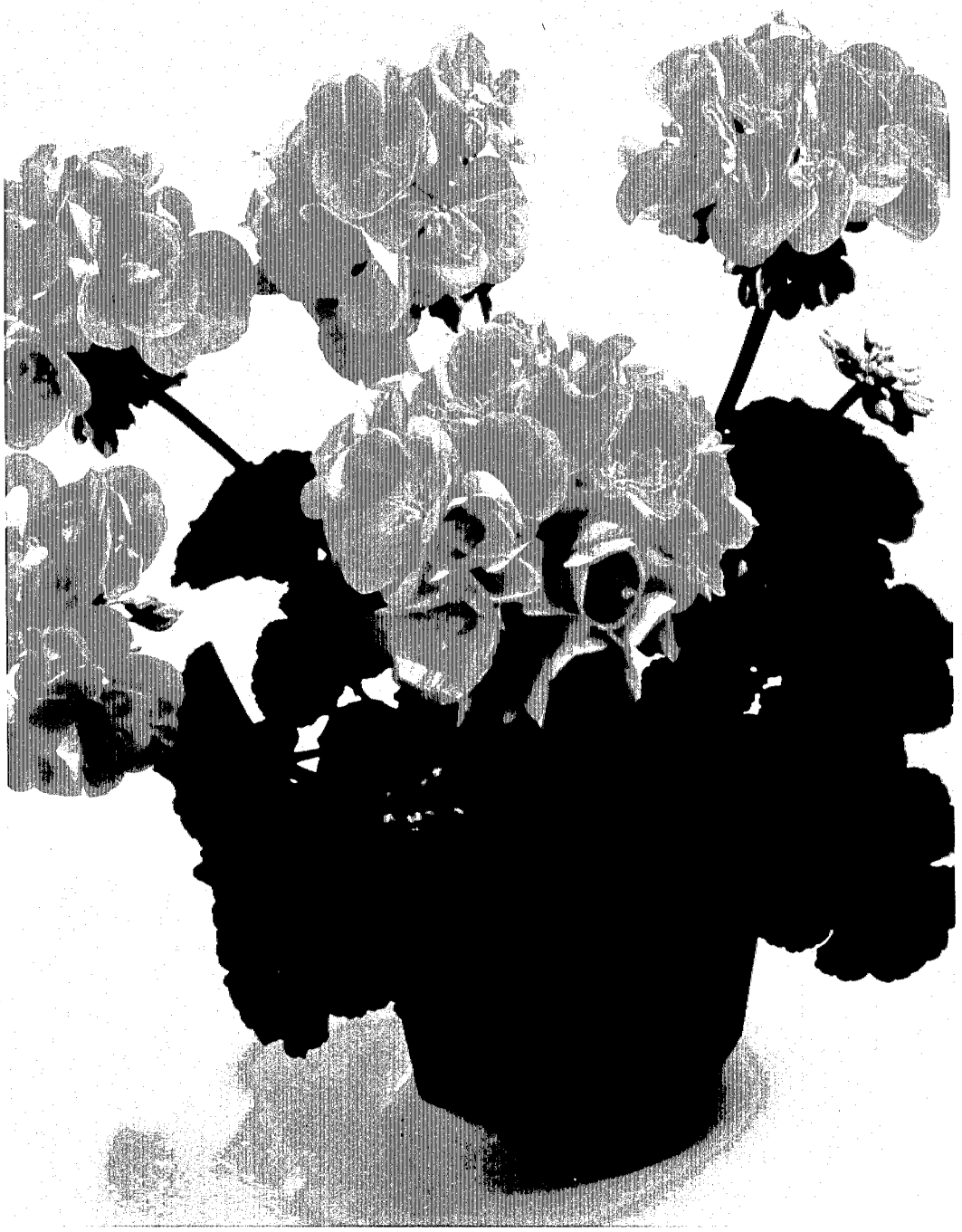

* * * * *